(12) United States Patent
Sakairi et al.

(10) Patent No.: US 8,500,981 B2
(45) Date of Patent: Aug. 6, 2013

(54) ELECTROPHORESIS APPARATUS AND ELECTROPHORESIS METHOD

(75) Inventors: Koji Sakairi, Taito-ku (JP); Satonari Akutsu, Taito-ku (JP); Yuji Maruo, Osaka (JP); Takateru Matsunaga, Osaka (JP); Yutaka Unuma, Osaka (JP); Atsunori Hiratsuka, Chiyoda-ku (JP); Hideki Kinoshita, Chiyoda-ku (JP); Nao Sakaguchi, Chiyoda-ku (JP); Kenji Yokoyama, Chiyoda-ku (JP)

(73) Assignees: Toppan Printing Co., Ltd., Tokyo (JP); Sharp Kabushiki Kaisha, Osaka (JP)

( * ) Notice: Subject to any disclaimer, the term of this patent is extended or adjusted under 35 U.S.C. 154(b) by 216 days.

(21) Appl. No.: 13/054,271

(22) PCT Filed: Jul. 15, 2009

(86) PCT No.: PCT/JP2009/062782
§ 371 (c)(1),
(2), (4) Date: Jan. 14, 2011

(87) PCT Pub. No.: WO2010/008008
PCT Pub. Date: Jan. 21, 2010

(65) Prior Publication Data
US 2011/0114485 A1 May 19, 2011

(30) Foreign Application Priority Data
Jul. 15, 2008 (JP) ................. 2008-184104

(51) Int. Cl.
*G01N 27/447* (2006.01)
*G01N 27/453* (2006.01)

(52) U.S. Cl.
USPC .......................... 204/466; 204/616

(58) Field of Classification Search
USPC .................. 204/456, 466, 606, 616
See application file for complete search history.

(56) References Cited

U.S. PATENT DOCUMENTS

| | | | |
|---|---|---|---|
| 5,464,515 A * | 11/1995 | Bellon | 204/466 |
| 2007/0045118 A1 | 3/2007 | Maruo et al. | |
| 2007/0151854 A1 | 7/2007 | Curcio | |
| 2007/0278102 A1 | 12/2007 | Hayashida et al. | |
| 2008/0053829 A1 | 3/2008 | Hayashida et al. | 204/600 |

FOREIGN PATENT DOCUMENTS

| | | |
|---|---|---|
| CN | 1987446 A | 6/2007 |
| JP | 58-53745 | 3/1983 |
| JP | 59-107253 | 6/1984 |
| JP | 63-138250 A | 6/1988 |

(Continued)

OTHER PUBLICATIONS

JPO English language abstract of Mukai et al. JP 04042050 A, application published Feb. 12, 1992.*

(Continued)

*Primary Examiner* — Alex Noguerola
(74) *Attorney, Agent, or Firm* — Nixon & Vanderhye, PC

(57) ABSTRACT

An electrophoresis apparatus includes a sample separating section for containing a sample separating medium for separating a sample in a horizontal direction, the sample separating section containing the sample separating medium in such a manner that the sample separating medium has an exposed portion at least one end of a surface of the sample separating medium, the surface being in parallel with the horizontal direction; and medium connecting means for connecting a sample containing medium to the sample separating medium at a connecting region, the sample containing medium containing a sample, and the connecting region satisfying a particular equation. By this, an electrophoresis technique with better accuracy than conventional arts can be provided.

15 Claims, 11 Drawing Sheets

FOREIGN PATENT DOCUMENTS

| | | | |
|---|---|---|---|
| JP | 04-042050 A | * | 2/1992 |
| JP | 2004-069387 | | 3/2004 |
| JP | 2006-258685 A | | 9/2006 |

OTHER PUBLICATIONS

Full English language translation of Mukai et al. JP 04042050 A, patent published Feb. 12, 1992.*

Full English language translation of Yoshida et al. JP 58-053745 A, patent published Mar. 30, 1983.*

Full English language translation of Yoshida et al. JP 59-107253 A, patent published Jun. 21, 1984.*

Hiratsuka, A. et al.; "*Fully Automated Two-Dimensional Electrophoresis System for High-Throughput Protein Analysis*"; Analytical Chemistry; vol. 79; No. 15; pp. 5730-5739; Aug. 1, 2007.

International Search Report for PCT/JP2009/062782.

European Search Report dated Mar. 13, 2012 for European Patent Application No. 09797933.0.

Chinese Office Action issued in Chinese Application No. 200980127615.8 dated Jan. 15, 2013 with English Translation.

* cited by examiner

ELECTROPHORESIS APPARATUS AND ELECTROPHORESIS METHOD

This application is the U.S. national phase of International Application No. PCT/JP2009/062782, filed 15 Jul. 2009, which designated the U.S. and claims priority to Japanese Patent Application No. 2008-184104, filed 15 Jul. 2008, the entire contents of each of which are hereby incorporated by reference.

TECHNICAL FIELD

The present invention relates to an automated biological sample separating apparatus, an apparatus constituting the automated biological sample separating apparatus, and use thereof. More specifically, the present invention relates to an automated electrophoresis apparatus and an automated electrophoresis method.

BACKGROUND ART

After the accomplishment of the human genome projects, ardent researches have been carried out on proteome. The term "proteome" encompass any proteins which are produced via translation in certain cells, organs, etc. One example of the researches on proteome is profiling of a protein.

One of most common techniques for profiling a protein is 2-dimension electrophoresis of the protein. Proteins have different electric charges and molecular weights unique to themselves. From proteome, which is a mixture of many kinds of proteins, the proteins may be separated based on the electric charges or molecular weights. However, it is possible to perform protein separation from the proteome with higher resolution for more kinds of the proteins by separating the proteins from the proteome based on electric charges and molecular weights in combination.

The 2-dimensional electrophoresis include two electrophoresis steps: isoelectric focusing electrophoresis for separating proteins based on their electric charge differences; and slab gel electrophoresis (especially, SDS-PAGE) for separating the proteins based on their molecular weight differences. Moreover, the 2-dimensional electrophoresis may be carried out with a sample prepared with or without a denaturing agent. As such, the 2-dimensional electrophoresis is an excellent technique capable of separating several hundreds kinds of proteins in one time.

In the 2-dimensional electrophoresis, a sample is subjected to the isoelectric focusing electrophoresis in a first dimension gel. Then, the first dimension gel is transferred to be applied to a second dimension gel in which the sample is subjected to the molecular-weight-based separation. Generally, the first dimension gel for the isoelectric focusing electrophoresis is very thin in comparison with its width and length. Therefore, it is difficult to recognize which side is the front side or back side of the gel, and in which way the gel has a pH gradient. Further, the gel is easy to be warped or twisted and thus is poor in shape stability. This would be a cause of poor reproducibility of results of the electrophoresis. Further, handling of the first dimension gel is not easy, which poses an impediment to an effort of improving the transfer of the first dimension gel to the second dimension gel in terms of positioning accuracy. Moreover, in case where the second dimension separation is carried out with SDS-PAGE, it is required to perform equilibrating (SDS treatment and reduction) treatment (chemical treatment) to the first dimension gel after the first dimensional electrophoresis, so that the proteins in the first dimension gel will be able to migrate through the second dimension gel. Due to the need of such treatment to the first dimension gel, the 2-dimensional electrophoresis produces different results depending on operator's proficiency.

As described above, the 2-dimensional electrophoresis is an excellent technique, yet it requires the operator thereof to be highly skilled in operating it. The dependency of the operator's proficiency makes it difficult for the 2-dimensional electrophoresis to obtain quantitative data with good reproducibility.

In order to overcome this problem, techniques to automate the 2-dimensional electrophoresis have been developed (see Patent Literature 1 and Non-Patent Literature 1).

CITATION LIST

Patent Literature

Patent Literature 1
Japanese Patent Application Publication, Tokukai, No. 2007-64848 A (Publication Date: Mar. 15, 2007)

Non Patent Literature

Non Patent Literature 1
Hiratsuka et al., Fully Automated Two-Dimensional Electrophoresis System for High-Throughput Protein Analysis, Anal. Chem., 79 (15), 5730-5739, 2007

SUMMARY OF INVENTION

Technical Problem

As described above, it has been a huge demand for higher spotting accuracy in the electrophoresis for analyzing a biological sample. In response to this, there is a need for an electrophoresis technique that can achieve a higher accuracy than the techniques of Patent Literature 1 and Non-Patent Literature 1.

The present invention is accomplished in view of the aforementioned problems, and a main object of the present invention is to provide an electrophoresis technique with higher accuracy than conventional arts.

Solution to Problem

In order to attain the object, an electrophoresis apparatus according to the present invention includes: a sample separating section for containing a sample separating medium for separating a sample in a horizontal direction, the sample separating section containing the sample separating medium in such a manner that the sample separating medium has an exposed portion at least one end of a surface of the sample separating medium, the surface being in parallel with the horizontal direction; and medium connecting means for connecting a sample containing medium to the sample separating medium at a connecting region, the sample containing medium containing a sample, and the connecting region satisfying the following equation (1):

$$Y \geq 0.4 \times X \quad (1),$$

where X is a distance in the horizontal direction from an inside end of the exposed portion exposed on an upper surface of the sample separating medium, to a proximal end of the connecting region to the sample separating section, and Y is a distance in a vertical direction.

With this arrangement, the sample containing medium containing the sample can be connected, at an appropriate position, with the sample separating medium for separating the sample. Thus, it is possible to improve accuracy of spots obtained as a result of the electrophoresis, compared to the conventional arts.

The electrophoresis apparatus according to the present invention may be preferably arranged such that the sample separating medium has a supporting section whose top reaches a height equal to or higher than the inside end of the exposed portion, and the connecting region is on the supporting section.

With this arrangement, the medium connecting means connects the sample containing medium to the sample separating medium in such a way that the electrophoresis will move the sample away from where the supporting section is located. Thus, the presence of the supporting section, surprisingly, improves the electrophoresis. Note that, for example in case where the exposed portion has a flat top, the exposed portion of the sample separating medium is deformed by the sample containing medium pushed against a non-terminal-side portion of the exposed portion, so that a terminal-side portion of the exposed portion serves as the supporting section (see FIG. 3(b)).

The electrophoresis apparatus according to the present invention may be preferably arranged such that the sample separating section has two plates being parallel with each other, for holding the sample separating medium therebetween.

With this arrangement, the sample separating medium has a board-like shape defined by the flat surfaces parallel with each other. As a result, the electrophoresis can perform more appropriate sample separation.

The electrophoresis apparatus according to the present invention may be arranged such that the sample containing medium and the sample separating medium are a gel or gels that contain(s) a gelling agent selected from the group consisting of polyacrylic amides, agarose, agar, and starch.

With this arrangement, the use of such a gel or gels leads to more appropriate sample separation.

The electrophoresis apparatus according to the present invention may be arranged such that the sample containing medium is higher in viscoelasticity than the sample separating medium. In other words, it is preferable that the sample separating medium and the sample containing medium be respectively configured to have such structural strengths that the sample containing medium will not deformed but the sample separating medium will be deformed when the sample containing medium is connected to the sample separating medium.

With this arrangement, the sample separating medium will be deformed without deforming the sample containing medium when the sample containing medium is connected to the sample separating medium. Thus, it becomes possible to push the sample containing medium into the sample separating medium appropriately.

The electrophoresis apparatus according to the present invention may be arranged such that it further includes: a first buffer tank containing at least part of the exposed portion; and a second buffer tank being located in such a manner that the sample separating section will be in between the second buffer tank and the exposed portion, the sample separating section having a communicating opening for communicating between the sample separating medium and the second buffer tank.

With this arrangement, in which the buffer tanks are provided, which are respectively connected with both the ends of the sample separating medium, it is possible to easily perform the electrophoresis.

The electrophoresis apparatus according to the present invention may be arranged such that it includes a structure in which the sample separating section, the first buffer tank, and the second buffer tank are integrated.

With this arrangement, in which the sample separating section, the first buffer tank, and the second buffer tank are integrated in a single unit, it is easy to handle them.

The electrophoresis apparatus according to the present invention may be arranged such that it further includes: a cap for medium shaping, the cap being detachably provided so as to cover the exposed portion of the sample separating medium in the first buffer tank; and a seal for medium shaping, the seal sealing the communication opening.

With this arrangement in which the cap for medium shaping and the seal for medium shaping are provided, the sample separating medium can be easily cast into a shape in the sample separating section by using the cap and seal.

The electrophoresis apparatus according to the present invention may be arranged such that the first buffer tank and the cap are configured such that, when the cap is attached inside the first buffer tank, the first buffer tank still has a space for holding a liquid.

With this arrangement, the cap for medium shaping does not fill up the first buffer tank. Thus, the cap can be easily removed from the first buffer tank. Moreover, for example in case where the sample separating medium is an acrylic amide gel, which solidified under anaerobic conditions, it is not preferable that the cap fills up the first buffer tank, because the gel would be solidified in a gap between the cap and the first buffer tank. In the present embodiment, however it is configured that the cap does not fill up the first buffer tank wholly, thereby preventing the solidification of the gel in the gap.

The electrophoresis apparatus according to the present invention may be preferably arranged such that the sample separating section has a first engaging section and the cap has a third engaging section, wherein the first engaging section and the third engaging section are configured to engage together, and the first buffer tank has a second engaging section and the cap has a fourth engaging section, wherein the second engaging section and the fourth engaging section are configured to engage together.

With this arrangement, it is possible to easily secure the cap to the electrophoresis apparatus.

The electrophoresis apparatus according to the present invention may be preferably arranged such that: the first engaging section and the third engaging section are configured to engage with each other by being configured that the first engaging section has a protrusion section and the third engaging section has a recess section corresponding to the protrusion section, or by being configured that the first engaging section has a recess section and the third engaging section has a protrusion section corresponding to the recess section, and the second engaging section and the fourth engaging section are configured to engage with each other by being configured that the second engaging section has a protrusion section and the fourth engaging section has a recess section corresponding to the protrusion section, or by being configured that the second engaging section has a recess section and the fourth engaging section has a protrusion section corresponding to the recess section. It is preferable that the engagement between the first engaging section and the third engaging section be different in depth from the engagement between the second engaging section and the fourth engaging section.

With this arrangement, the second engaging section and the fourth engaging section can be engaged smoothly even after the engagement of the first engaging section and the third engaging section, in the case where the engagement of the second engaging section and the fourth engaging section is deeper than the engagement of the first engaging section and the third engaging section. Alternatively, in the case where the first engaging section and the third engaging section is deeper than the engagement of the engagement of the second engaging section and the fourth engaging section, the first engaging section and the third engaging section can be engaged smoothly even after the engagement of the second engaging section and the fourth engaging section. In this way, the engagement of one pair of the engaging sections can be performed after the engagement of the other pair of the engaging sections, while letting the air out of the sample separating medium. Thus, the shaping of the sample separating medium can be performed appropriately.

The electrophoresis apparatus according to the present invention may be preferably arranged such that: the cap has an overlapping section for being overlapped with a surface of the sample separating section or a side wall of the first buffer tank.

With this arrangement, the overlapping section does not allow the air to enter inside the cap, thereby making it possible to perform the shaping of the sample separating medium appropriately.

The electrophoresis apparatus according to the present invention may be preferably arranged such that: the overlapping section has an overlapping width of at least 1 mm.

With this arrangement, in which the overlapping section has an overlapping width of at least 1 mm, it is made more difficult for the air to enter inside the cap. Thus, it is possible to perform the shaping of the sample separating medium more appropriately.

The electrophoresis apparatus according to the present invention may be preferably arranged such that the communicating opening is located on an upper surface of the sample separating section.

With this arrangement, in which the communicating opening is located on the upper surface of the sample separating section, the seal for sealing the communicating opening is also attached onto the upper surface of the sample separating section. Thus, it is so convenient that the seal can be easily removed from the sample separating section.

The electrophoresis apparatus according to the present invention may be preferably arranged such that the sample separating medium having a bulged portion being bulged downward and located on a distal side to the exposed section and in a region ranged from the communicating opening to an edge of the sample separating medium.

With this arrangement, the bulged portion is located closer to the edge of the sampling separating medium than the communicating opening is. Thus, the location of the bulged portion does not impede the sample separation in the sample separating medium. The bulged portion lets the sample separating medium have a heavier weight. In dissembling of the sample separating section for removal of the sample separating medium, this facilitates the sample separating medium to be remained in a lower part of the sample separating section. Moreover, by letting the sample separating medium contain an electrolyte, it becomes possible to supply the electrolyte from the bulged portion.

A method according to the present invention for performing electrophoresis includes: connecting a sample separating medium with a sample containing medium at a connecting region, (i) the sample separating medium being configured to separate a sample in a horizontal direction and being held in an insulating member in such a manner that the separating medium has an exposed portion at least one end of a surface of the sample separating medium, (ii) the sample containing medium containing the sample, and the connecting region satisfying the equation (1):

$$Y \geq 0.4 \times X \quad (1),$$

where X is a distance in the horizontal direction from an inside end of the exposed portion exposed on an upper surface of the sample separating medium, to a proximal end of the connecting region to the sample separating section, and Y is a distance in a vertical direction.

Further, the method according to the present invention may be preferably arranged such that the sample separating medium has a supporting section whose top reaches a height equal to or higher than the inside end of the exposed portion, and the connecting region is on the supporting section.

There arrangements can bring about the same effects as the electrophoresis apparatus according to the present invention.

Advantageous Effects of Invention

With the electrophoresis technique according to the present invention, a sample separating medium for separating a sample can be connected, at an appropriate position, with a sample containing medium for containing the sample. Therefore, the electrophoresis technique according to the present invention can achieve a higher accuracy than the conventional arts.

DESCRIPTION OF EMBODIMENTS

Figure 1:
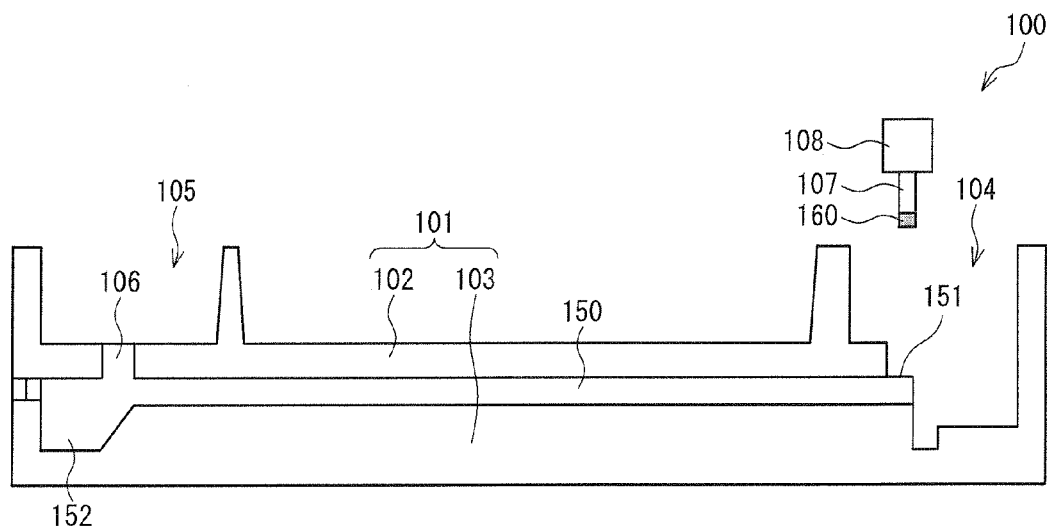
FIG. 1 is a cross sectional view schematically illustrating a configuration of an electrophoresis apparatus according to one embodiment of the present invention.
Figure 2:
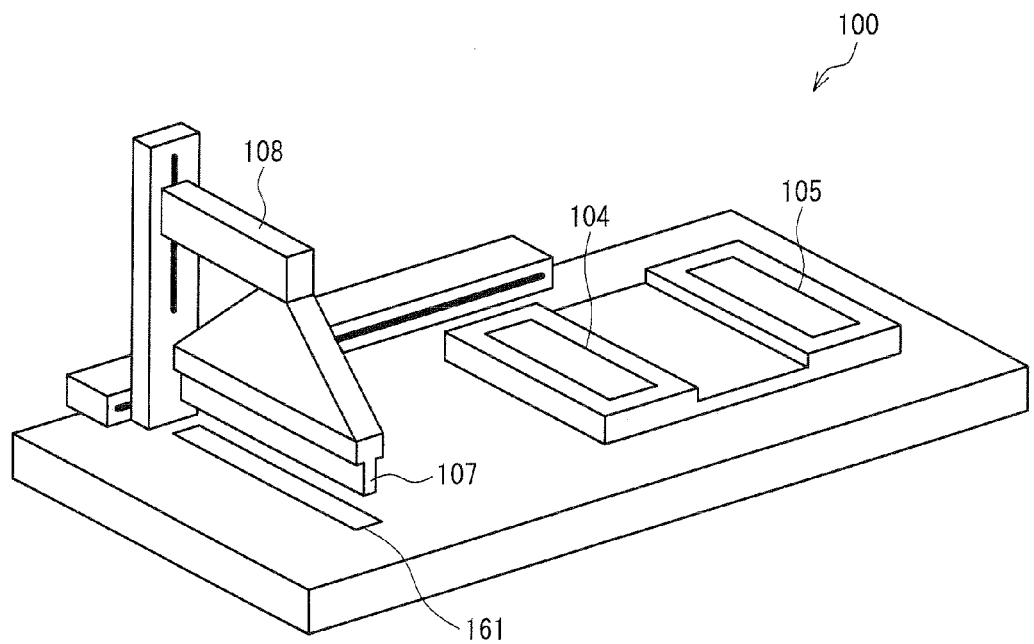
FIG. 2 is a perspective view schematically illustrating a configuration of the electrophoresis apparatus according to the embodiment of the present invention.

FIG. 1 is a cross sectional view schematically illustrating a configuration of an electrophoresis apparatus 100 according to one embodiment of the present invention. FIG. 2 is a perspective view schematically illustrating a configuration of the electrophoresis apparatus 100. As illustrated in FIG. 1, the electrophoresis apparatus 100 is configured such that a sample separating section 101 including a first plate 102 and a second plate 103 parallel with the first plate holds a sample separating medium 150 therebetween. The sample separating medium 150 is a medium in which a sample is to be separated in a horizontal direction along the medium. The sample separating section 101 holds the sample separating medium 150 in such a manner that a portion (an exposed portion 151) of the sample separating medium 150 is exposed at one edge of a surface parallel with the horizontal direction. The term "inside end of the exposed portion (exposed part)" used in this Description intends to mean that portion of the sample separating medium which is exposed and is in contact with a sample separating section.

Moreover, the electrophoresis apparatus 100 has a first buffer tank 104 and a second buffer tank 105. At least part of the exposed portion 151 is inserted inside the first buffer tank 104. The second buffer tank 105 is located in such a manner that the sample separating section 101 is in between the second buffer tank 105 and the exposed section 151. The first plate 102 of the sample separating section 101 has a communicating opening 106 for communicating between the sample separating medium 150 and the second buffer tank 105.

The sample separating medium 150 has a bulged portion 152 in a region ranged from the communicating opening 106 to an edge of the sample separating medium 150 and on a distal side to the exposed section 151. The bulged portion 152 is bulged downward.

Moreover, the electrophoresis apparatus 100 includes medium connecting means including a holding section 107 and a transporting arm 108. The holding section 107 supports a sample containing medium 160 in which a sample is contained. The transporting arm 108 is configured to move the holding section 107. In one embodiment, the transporting arm 108 is a transporting arm capable of moving the holding section 107 in 2-dimensional directions as illustrated in FIG. 2, and is configured to transfer the sample containing medium 160 from a sample containing medium storage site 161 to a position where the sample containing medium 160 is connected with the sample separating medium 150.

As illustrated in FIG. 1, the sample separating section 101, the first buffer tank 104, and the second buffer tank 105 may be integrated in a single structure, so that the single structure can be used as a chip for use in electrophoresis.

The first plate 102 and the second plate 103 may be made from an insulating material such as an acrylic material, glass, etc. The sample separating section 101 is configured such that the first plate 102 and the second plate 103 are adhered together so as to hold the sample separating medium 150 therebetween. After electrophoresis is performed with the sample separating section 101, the first plate 102 and the second plate 103 are taken off from the sample separating section 101 by using a tool such as a spatula. Thereby, the sample separating medium 150 is removed from the sample separating section 101 so as to be subjected to a subsequent analysis. The first plate 102 and the second plate 103 may be adhered together with a general adhesive, but it is preferable to adhere the first plate 102 and the second plate 103 by ultrasonic welding because the ultrasonic welding is free from dispersion of the adhesive, and the like problems.

The second plate 103 is extended as long as the sample separating medium 150. Therefore, when the first plate 102 and the second plate 103 are separated from each other, the sample separating medium 150 can be easily remained on the second plate 103. That is, it is the second plate 103 that supports a lateral side of the sample separating medium 101 (not illustrated). Moreover, as described above, the sample separating medium 150 has the bulged portion 152, thereby making it easier to remain the sample separating medium 150 on the second plate 103. Because the subsequent analysis is supplied with the sample separating medium 150 in such a form that it is remained on the second plate 103, the subsequent analysis can be performed in a fixed manner.

The sample containing medium 160 and the sample separating medium 150 may be any kind of media that are generally used for electrophoresis. For example, the sample containing medium 160 and the sample separating medium 150 may be a gel or gels that contain(s) a gelling agent selected from the group consisting of polyacrylic amides, agarose, agar, and starch.

The sample containing medium 160 contains a sample to be subjected to the electrophoresis. The sample may be uniformly distributed throughout the sample containing medium 160. However, a primary electrophoresis may be performed on the sample containing medium 160.

Figure 3:
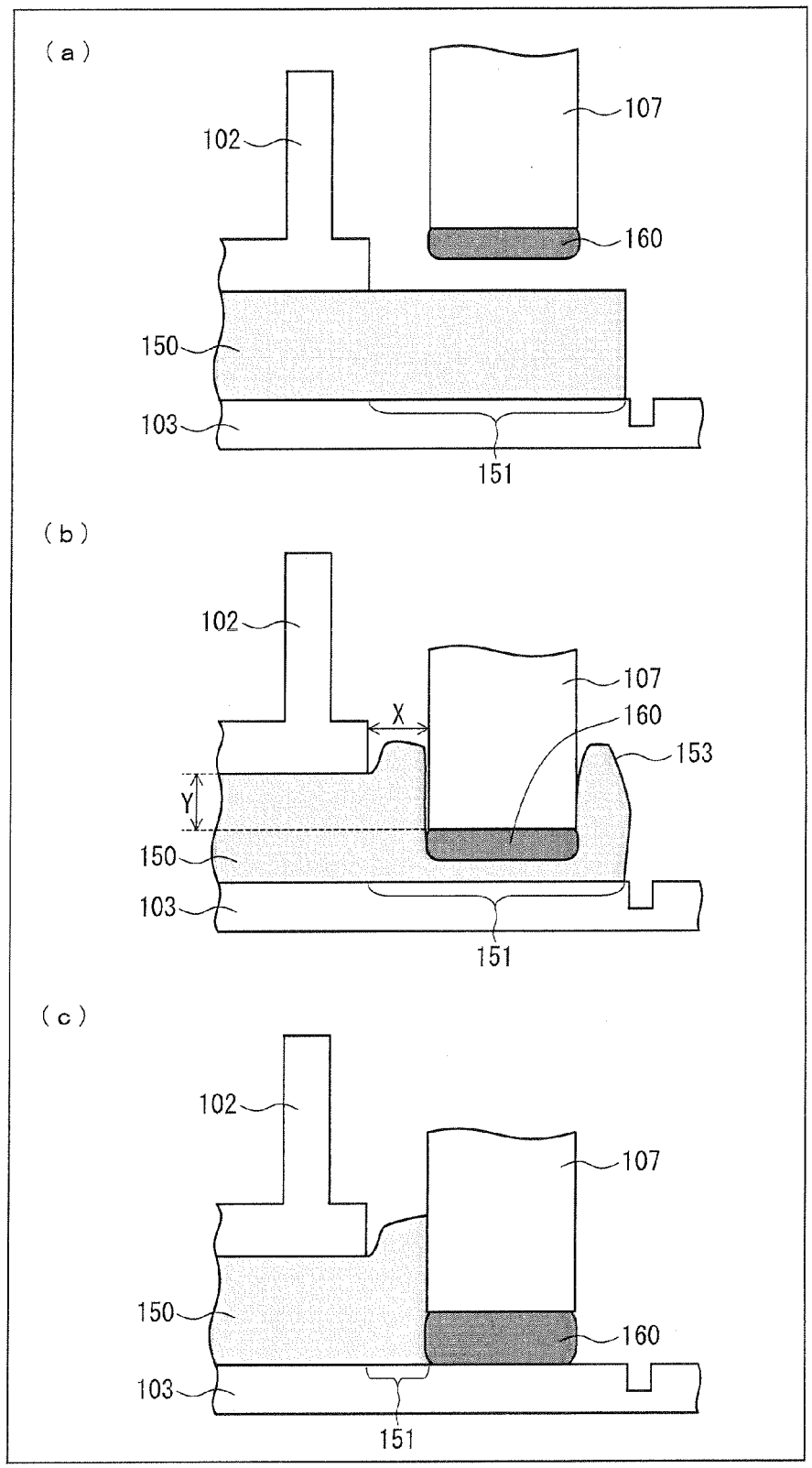
FIG. 3 is a schematic view illustrating a variation of a way connecting a sample containing medium and a sample separating medium in the electrophoresis according to one embodiment of the present invention.

The sample containing medium 160 is connected with the exposed section 151 of the sample separating medium 150 as illustrated in FIG. 3. Moreover, in one embodiment, the sample containing medium 160 is transferred on top of the exposed portion 151 as illustrated in FIG. 3(a), then the sample containing medium 160 is pushed into the exposed portion 151 downwardly, so that the sample containing medium 160 and the exposed portion 151 are connected with each other (media connecting step). When connected with each other the sample containing medium 160 and the exposed portion 151 are connected via a connecting region satisfying the following equation (1). By this, it becomes possible to appropriately transfer the sample from the sample containing medium 160 to the sample separating medium.

$$Y \geq 0.4 \times X \tag{1},$$

where X is a horizontal distance from an inside end of the exposed portion 151 to the sample containing medium 160, and Y is a distance in a vertical direction.

Moreover, it is preferable that the sample separating medium 150 have a supporting section 153 whose top reaches a height equal to or higher than the inside end of the exposed portion 151 as illustrated in FIG. 3(b), and that the connecting region is located on the supporting section 153, as illustrated in FIG. 3(b). For example, a configuration in which the connecting region is on the supporting section 153 as illustrated in FIG. 3(b) is more preferable than a configuration in which the connecting region is out of the supporting section 153 as illustrated in FIG. 3(c).

Moreover, it is preferable that the sample containing medium 160 be higher in viscoelasticity than the sample separating medium 150. In other words, it is preferable that the sample separating medium 150 and the sample containing medium 160 are respectively differentiated in terms of their structural strength such that the sample containing medium 160 will not be deformed but the sample separating medium 150 will be deformed, when the sample separating medium 150 is attached to the sample containing medium 160. With this configuration, it becomes possible to appropriately deform the supporting section 153 as illustrated in FIG. 3. For differentiating the sample separating medium 150 and the sample containing medium 160 in terms of viscoelasticity and structural strength, the sample separating medium 150 and the sample containing medium 160 may be adjusted in viscoelasticity and structural strength by, for example, preparing the sample separating medium 150 and the sample containing medium 160 with different kinds of gelling agents, or more preferably, with an identical gelling agent in such different quantities that the sample containing medium 160 has a greater gelling agent content than the sample separating medium 150.

Figure 4:
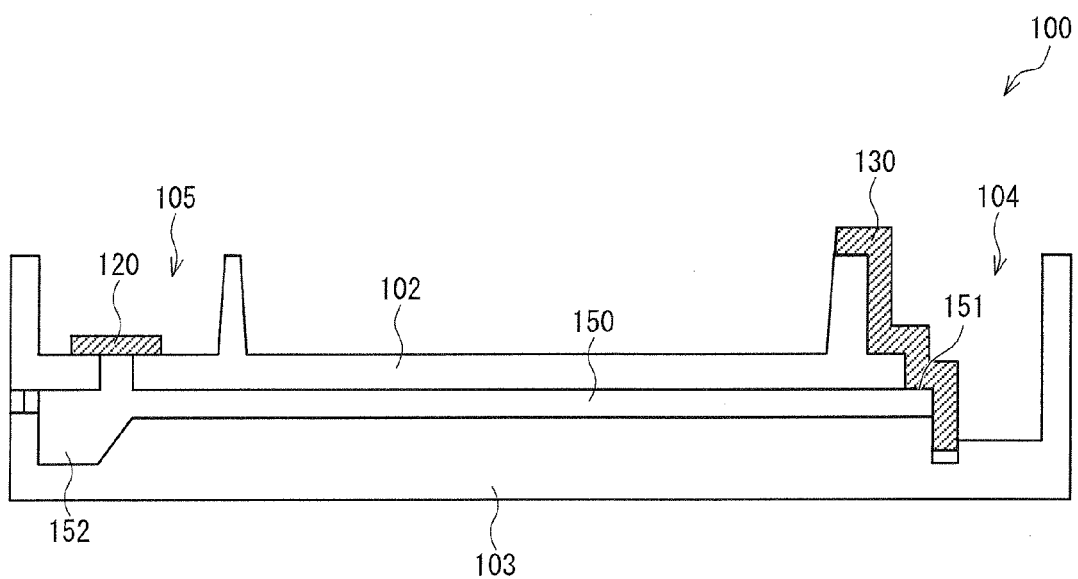
FIG. 4 is a cross sectional view schematically illustrating the electrophoresis apparatus according to one embodiment of the present invention as to formation of a 5 sample separating medium.

FIG. 4 is a cross sectional view schematically illustrating the electrophoresis apparatus according to one embodiment of the present invention as to formation of a sample separating medium. As illustrated in FIG. 4, the sample separating section 101 is sealed in such a manner that the exposed portion 151 is covered with a cap 130 for medium shaping and the communicating opening 106 is covered with a seal 120 for medium shaping. In this way, the sample separating medium 150 can be formed inside the sample separating section 101.

Here, the cap 130 does not fill up the first buffer tank 104. Thus, the cap 130 can be easily removed from the first buffer tank 104. Moreover, for example in case where the sample separating medium 150 is an acrylic amide gel, which solidified under anaerobic conditions, it is not preferable that the cap 130 fills up the first buffer tank 104, because the gel would be solidified in a gap between the cap 130 and the first buffer tank 104. In the present embodiment, however it is configured that the cap 130 does not fill up the first buffer tank 104 wholly, thereby preventing the solidification of the gel in the gap.

Figure 5:
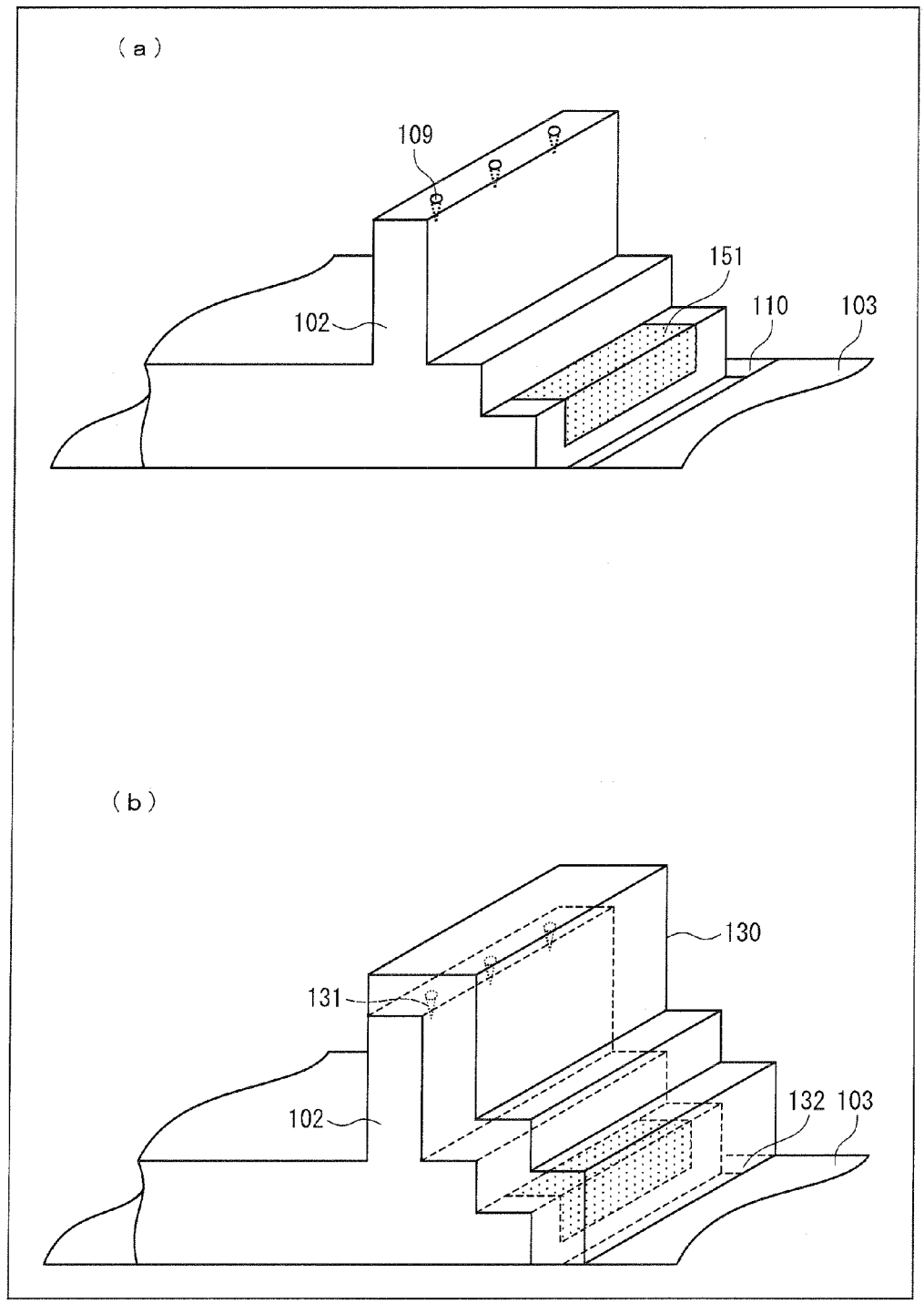
FIG. 5 is a perspective view schematically illustrating a configuration of a cap for medium shaping for the electrophoresis apparatus according to one embodiment of 10 the present invention.

FIG. 5 (a) is a perspective view illustrating shapes of the sample separating section 101 and the first buffer tank 104, with which the cap 130 for medium shaping is to be engaged. FIG. 5(b) is a perspective view schematically illustrating a configuration of the cap 130 for medium shaping. As illustrated in FIGS. 5(a) and 5(b), a recess section (first engaging section) 109 of the sample separating section 101 and a protrusion section (third engaging section) 131 of the cap 130 are to be engaged together. Meanwhile, a recess section (second engaging section) 110) of the first buffer tank 104 and a protrusion section (fourth engaging section) 132 of the cap 130 are to be engaged together. Because the engagement between the recess section 110 and the protrusion section 132 engages deeper than the engagement between the recess section 109 and the protrusion section 131, a user may firstly make the engagement between the recess section 110 and the protrusion section 132, and secondly make the engagement between the recess section 109 and the protrusion section 131. In this way, it is possible to engage the cap 130 with the sample separating section 101 and the first buffer tank 104 without allowing air to enter therein.

As illustrated in FIG. 5(b), the cap 130 has an overlapping section of 1 mm in width, which overlaps with a surface of the sample separating section 101 and a side wall of the first buffer tank 104. With this configuration, the cap 130 can be engaged with the sample separating section 101 and the first buffer tank 104, thereby preventing air from entering the gel after the engagement.

Calculation Example 1

Figure 6:
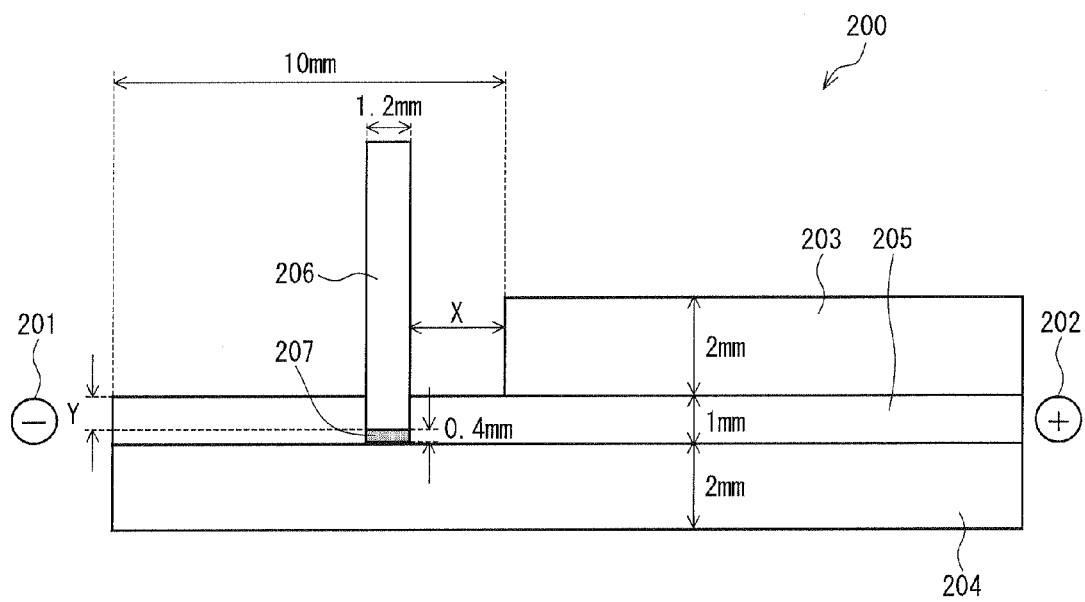
FIG. 6 is a cross sectional view illustrating a model of an electrophoresis apparatus used in Calculation Example 1.

To determine an appropriate connection position for the connection between the sample separating medium and the sample containing medium, computer simulation of an electrophoresis of a sample was carried out by using, as a model, an electrophoresis apparatus as illustrated in FIG. 6.

As illustrated in FIG. 6, the electrophoresis apparatus 200 was configured such that, between a cathode 201 and an anode 202 and, a gel (sample separating medium) 205 of 1 mm in thickness sandwiched between acrylic plates 203 and 204 of 2 mm in thickness was provided. The acrylic plate 203 was absent on a cathode 201 side, thereby exposing the gel 205 by 10 mm on the cathode 201 side. A gel (sample containing medium) 207 of 0.4 mm in thickness and 1.2 mm in width and supported by a supporter 206 was pushed into the exposed portion of the gel 205. Here, X was a distance between the gel 207 and a cathode-side end of the acrylic plate 203, the cathode-side end having been proximal to the cathode 201 (that is, X was a distance by which the sample traveled through the exposed gel 205), and Y was a distance between an upper side of the gel 205 and an upper side of the gel 207 (that is, Y was a distance by which the gel 207 was pushed into the gel 205).

The gels 205 and 207 had a dielectric constant equal to that of water. A sample (charged particles) tested herein was modeled lysozyme. Mobility of the model lysozyme was calculated out from actual measurement values of SDS-PAGE of lysozyme. It was assumed that the model lysozyme was to enter the gel (sample separating medium) 205 from eight (8) positions of the gel (sample containing medium) 207, where the eight positions were inner into the gel 205 by 0.02 mm from four corners of the gel 207 and midpoints of four sides of the gel 207, respectively.

Figure 7:
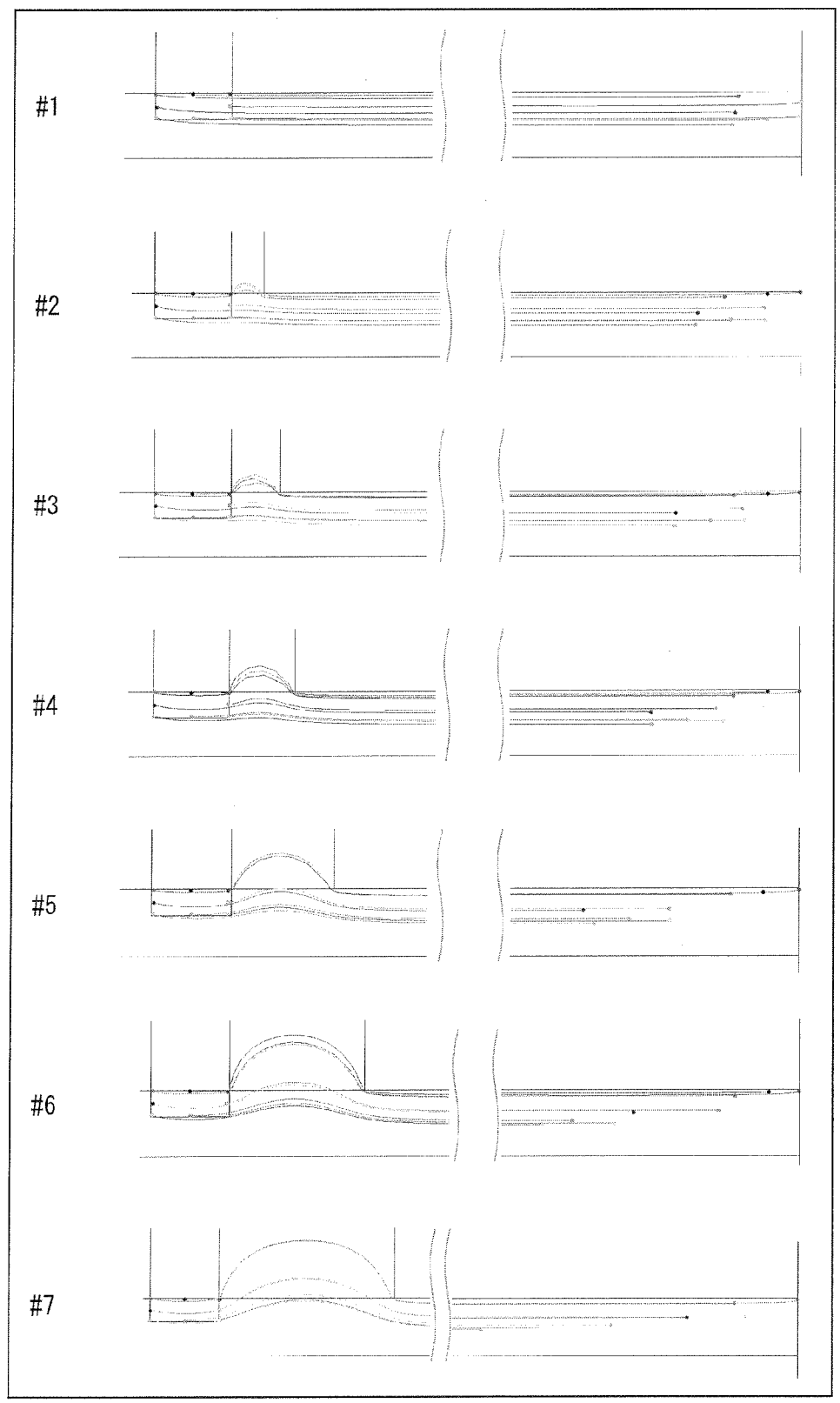
FIG. 7 is a view illustrating results of simulation in Calculation Example 1.
Figure 8:
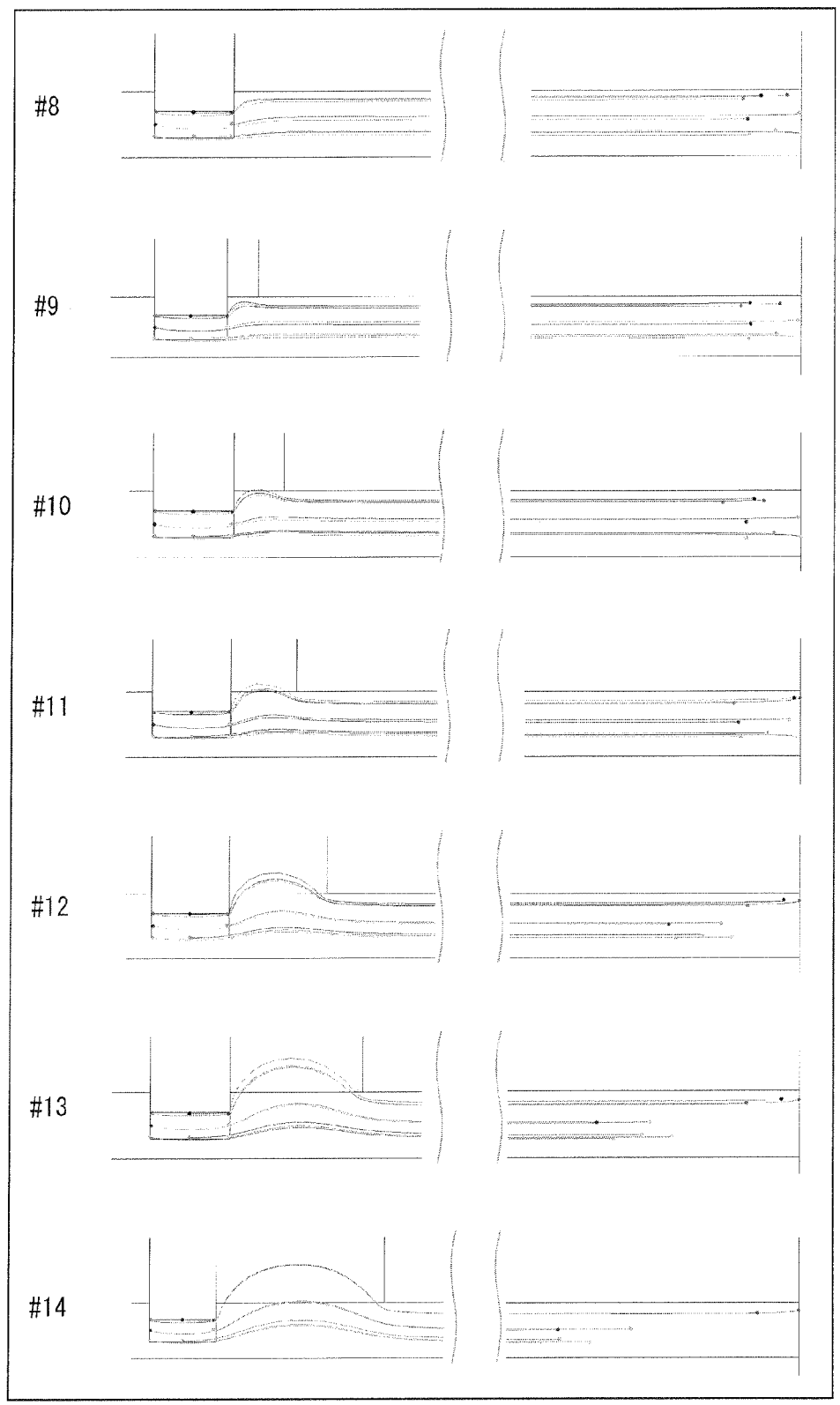
FIG. 8 is a view illustrating a simulation result in Calculation Example 1.
Figure 9:
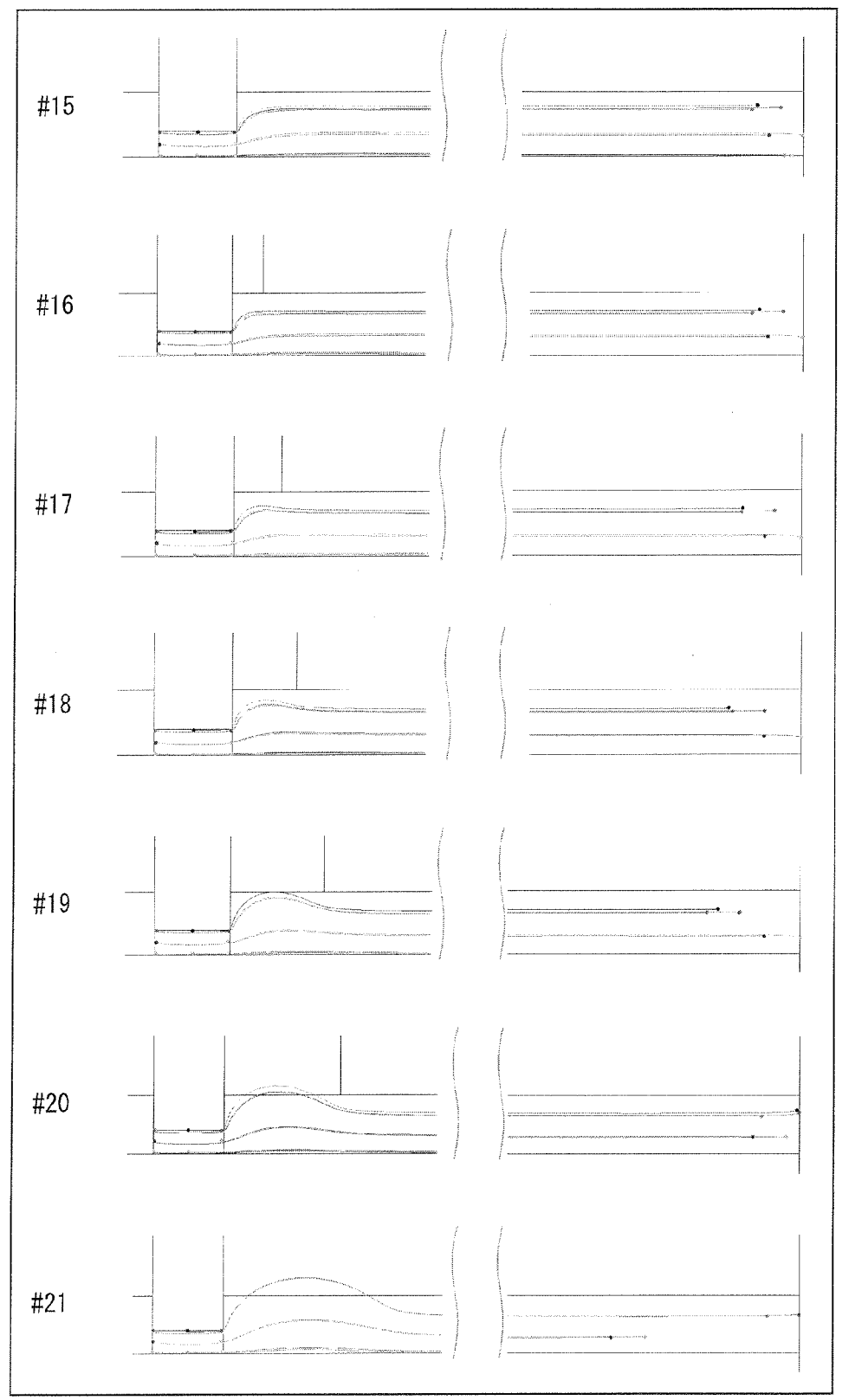
FIG. 9 is a view illustrating a simulation result in Calculation Example 1.
Figure 10:
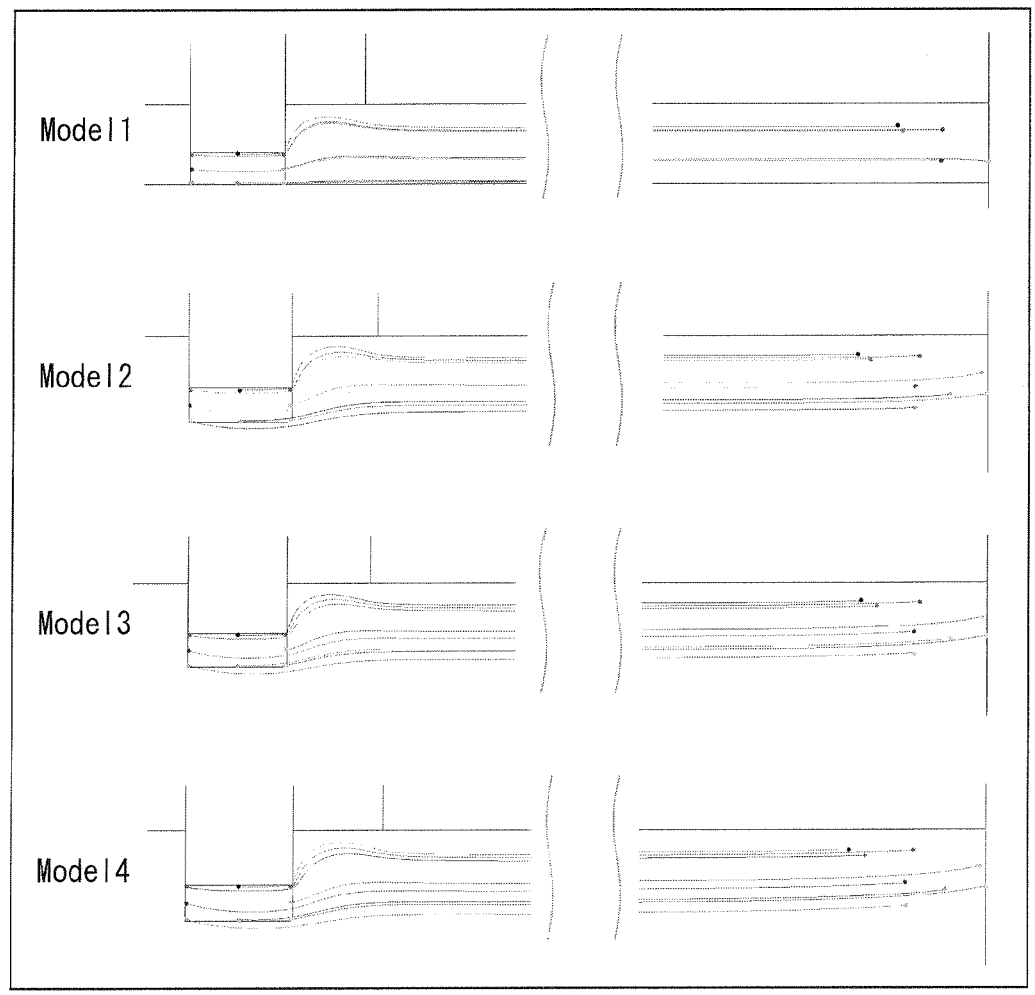
FIG. 10 is a view illustrating a simulation result in 25 Calculation Example 2.

FIG. 7 is a view illustrating results of simulation where Y was 0 mm and X was varied in a range of 0 to 3 mm. In FIG. 7, the left-hand side shows the movement of the modeled lysozyme in the vicinity of the position where the gel 207 was pushed in, while the right-hand side shows the movement of the modeled lysozyme in the vicinity of an anode-side end of the gel 205, the anode-side end having been proximal to the anode 202. FIGS. 8, 9, and 10 are illustrated in the same fashion.

When X=0 mm, the modeled lysozyme moved in the gel 205 but did not diffuse into the buffer, as shown in #1. The modeled lysozyme entered the gel 205 from the midpoint of the upper side of the gel 207 and the positions on the right-hand side of the gel 207 was blocked by a wall (acrylic plate 203) provided to the gel. When X=0.5 mm, 0.75 mm, 1 mm, 1.5 mm, or 2 mm, diffusion of the modeled lysozyme into the buffer was observed as shown in #2, #3, #4, or #6. Meanwhile, the modeled lysozyme was not blocked by the wall in these cases. When X=3 mm, as illustrated in #7, the diffusion of the modeled lysozyme into the buffer was observed. In this case, however, the modeled lysozyme from the middle of the upper side of the gel 207 as blocked by the wall (acrylic plate 203).

As described above, when Y=0 mm, the movement of the modeled lysozyme in the gel (sample separating medium) 205 was observed from all the positions of the gel (sample containing medium) 207 only in the case where X=0 mm.

FIG. 8 is a view illustrating results of simulation, where Y=0.3 mm and X was varied in the range of 0 to 3 mm.

When X=0 mm, 0.5 mm, or 0.75 mm, the movement of the modeled lysozyme in the gel 205 was observed but the modeled lysozyme did not diffuse into the buffer and also was not blocked by the acrylic plate. When X=1 mm, 1.5 mm or 2 mm, the modeled lysozyme was diffused into the buffer as shown in #11, #12, or #13. In these cases, the modeled lysozyme was not blocked by the wall. When X=3 mm, the diffusion of the modeled lysozyme into the buffer was observed as illustrated in #14, but the modeled lysozyme from the midpoint of the upper side of the gel 207 was blocked by the wall (acrylic plate 203).

As described above, when Y=0.3 mm, the movement of the modeled lysozyme in the gel (sample separating medium) 205 was observed from all the positions of the gel (sample containing medium) 207 only in the case where X=0.75 mm or less.

FIG. 9 is a view illustrating results of simulation where Y=0.6 mm and X was varied in a range of 0 to 3 mm.

When X=0 mm, the movement of the modeled lysozyme in the gel 205 was observed without the diffusion thereof into the buffer, as illustrated in #15. The modeled lysozyme from the left portion of the lower side of the gel 207 was blocked by the wall (acrylic plate 204). When X=0.5 mm, 0.75 mm, 1 mm or 1.5 mm, the movement of the modeled lysozyme in the gel 205 was observed without the diffusion thereof into the buffer, as illustrated in #16, #17, or #19. The modeled lysozyme from three positions on the lower side of the gel 207 was blocked by the wall (acrylic plate 204). When X=2 mm, the modeled lysozyme was diffused into the buffer, as illustrated in #20. Moreover, the modeled lysozyme from the three position on the lower side of the gel 207 was blocked by the wall (acrylic plate 204). When X=3 mm, as illustrated in #21, the modeled lysozyme was diffused into the buffer. Meanwhile, in this case, the modeled lysozyme from the midpoint of the upper side of the gel 207 was blocked by the wall (acrylic plate 203) and the modeled lysozyme from the three points on the lower side of the gel 207 was blocked by the wall (acrylic plate 204).

As described above, when Y=0.6 mm, the movement of the modeled lysozyme in the gel (sample separating medium) 205 was observed from all the positions of the gel (sample containing medium) 207 only in the case where X=1.5 mm or less.

Table 1 shows the above results. "○" indicates that the modeled lysozyme from all the points moved in the gel (sample separating medium 205) while "x" indicates that the modeled lysozyme from any of the points was diffused into the buffer.

TABLE 1

|  | X(mm) | | | | | | |
|---|---|---|---|---|---|---|---|
|  | 0 | 0.5 | 0.75 | 1 | 1.5 | 2 | 3 |
| Y = 0.0 mm | #1 ○ | #2 x | #3 x | #4 x | #5 x | #6 x | #7 x |
| Y = 0.3 mm | #8 ○ | #9 ○ | #10 ○ | #11 x | #12 x | #13 x | #14 x |
| Y = 0.6 mm | #15 ○ | #16 ○ | #17 ○ | #1 ○ | #1 ○ | #20 x | #21 x |

As illustrated in Table 1, favorable results were obtained when the connecting region via which the gel 207 and the gel 205 were connected satisfied the following Equation (1):

$$Y \geq 0.4 \times X \quad (1),$$

where X is a distance from the gel (sample containing medium) 207 to the acrylic plate (upper plate for gel) 203, and Y is a distance from the upper side of the gel 207 to the upper side of the gel (sample separating medium) 205.

Calculation Example 2

To analyze how the thickness of the gel 025 affected the results of the simulation in Calculation Example simulation was repeated based on the model in Calculation Example 1 but with different thicknesses of the gel 205.

FIG. 10 is a view illustrating results of simulation, where X=1 mm, Y=0.6 mm, and the thickness of the gel 205 was varied in the range of 1 to 9 mm. Models 1 to 4 respectively show the results of the simulation with the gel 205 of 1 mm, 3 mm, 6 mm, and 9 mm in thickness.

As shown in Models 1 to 4, no diffusion of the modeled lysozyme into the buffer was observed with the gel 205 of any of these thicknesses. In Model 1, the modeled lysozyme from three positions on the lower side of the gel 207 was blocked by the wall (acrylic plate 204). In Models 2 to 4, the thick thickness of the gel 205 prevented the modeled lysozyme from abutting the wall.

In Models 2 to 4 with the thick thickness of the gel 205, it was observed that the course of the movement of the modeled lysozyme showed large downward curves immediately after the modeled lysozyme moved out of the gel 207, compared with Model 1. It is deduced that the thick thickness of the gel 205 attributed to the peculiar movement with the large downward curves. In the vicinity of the gel 207, electric flux lines were blocked by the supported 206 and thereby curved downwardly. It is deduced that in Model 1, the acrylic plate 204 is located right under the gel 207, thereby preventing the downward curving of the electric flux lines, whereas the thick thickness of the gel 205 allows the electric flux lines to curve downwardly in the gel 205 right under the gel 207 in Models 2 to 4, thereby resulting in the downward course of the movement of the modeled lysozyme immediately after the modeled lysozyme moves out of the gel 207.

Therefore, it is considered that the course of the electrophoresis movement of the modeled lysozyme (sample) is not influence by the thickness of the gel (sample separating medium) 205.

Experiment Example 1

An electrophoresis apparatus according to the present invention was prepared as illustrated in FIG. 1. Electrophoresis was actually conduced by using the electrophoresis apparatus with various X and Y parameters. Separation of samples was detected by fluorescence. The sample containing medium was an IPG gel medium in which a first dimensional electrophoresis of mouse liver soluble proteins had been conducted.

Figure 11:
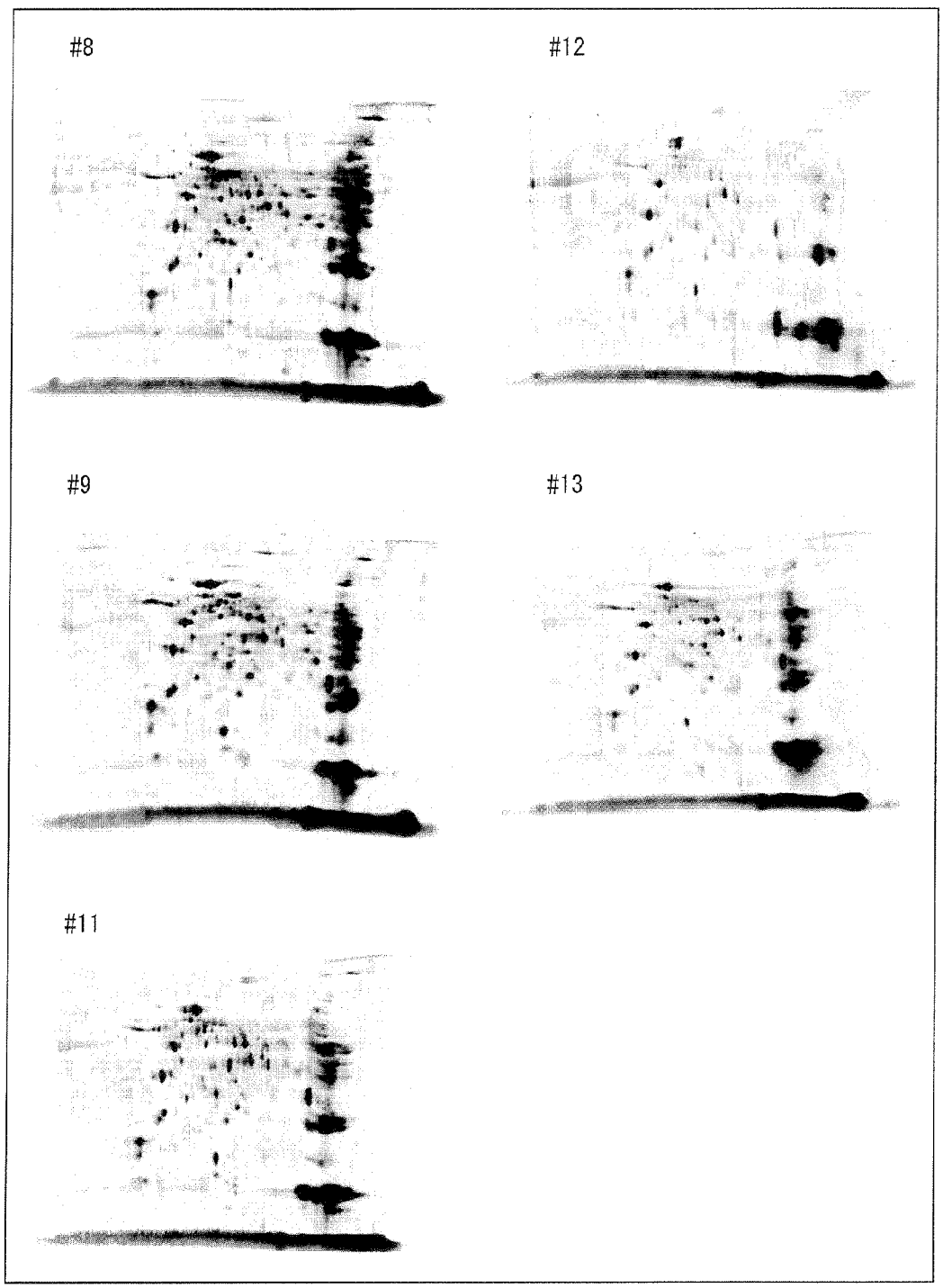
FIG. 11 is a view illustrating an electrophoresis result in Example 1.

FIG. 11 is a view illustrating fluorescent spots obtained as a result of the electrophoresis in which Y=0.3 mm and X was varied in a range of 0 to 2 mm. As illustrated in FIG. 11, there was a tendency that an increase in X caused a decrease in overall protein intensity. Moreover, when X and Y satisfied the Equation (1), that is, when X=0 mm or 0.5 mm, the spots showed no tailing as shown in #8 or #9. When X=1 mm, the spots showed slight tailing as shown in #11. On the other hand, in case where X and Y did not satisfy the Equation (1), that is, when X=1.5 mm or 2 mm, the spots showed tailing as shown in #12 or #13.

Experimental Example 2

Figure 12:
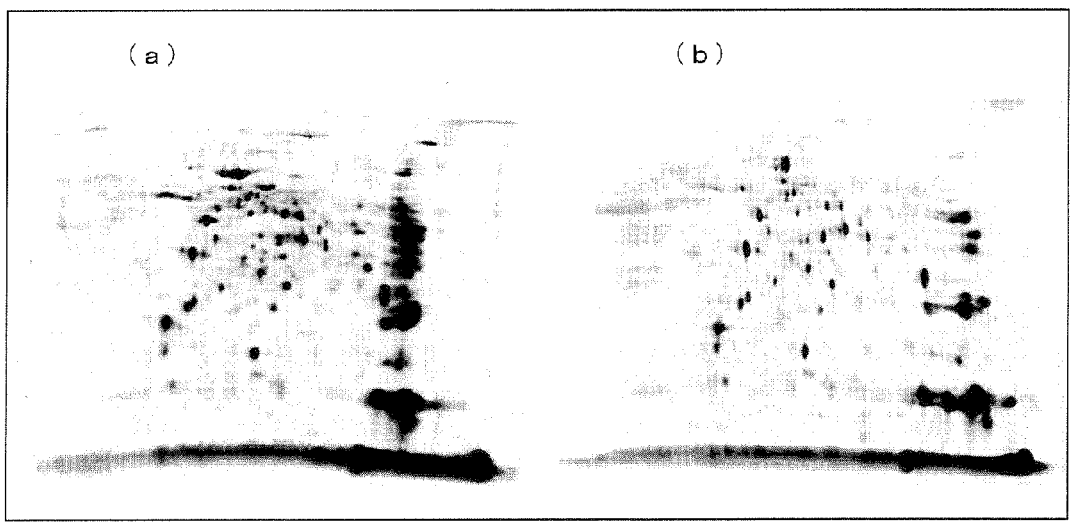
FIG. 12 is a view illustrating an electrophoresis result in Example 2.

An electrophoresis apparatus according to the present invention was prepared as illustrated in FIG. 1. Electrophoresis was actually conduced by using the electrophoresis apparatus. Separation of samples was detected by fluorescence. The sample containing medium was an IPG gel medium in which a first dimensional electrophoresis of mouse liver soluble proteins had been conducted. FIG. 12(*a*) shows results of electrophoresis using a connecting method (1 step) in which the supporting section 153 was formed as illustrated in FIG. 3(*b*). FIG. 12(*b*) shows results of electrophoresis using a connecting method (2 step) in which no support section was formed as illustrated in FIG. 3(*c*). As illustrated in FIG. 12, the result was better in the configuration in which the sample containing medium was connected vertically to the sample separating medium along a direction perpendicular to a direction in which the sample was separated, than in the configuration (2 step) in which the sample containing medium was connected sideways to the sample separating medium along the direction in which the sample was separated.

Further, the respective images of the results were detected by using Typhoon (GE healthcare), and subjected to image processing by PDQuest (BioRad). Then, by using ProFinder (Perkin Elmer), each spot was detected and analyzed in terms of its spot fluorescence intensity and spot gravity point. From coordinates of the spot gravity, a peak top position and a half-value width of the spot were determined. Table 2 shows results of the analysis.

TABLE 2

|      | 1 step | | 2 step | |
|------|---------------|----------|---------------|----------|
| spot | Y half-value width | C V | Y half-value width | C V |
| #1 | 9.75 | 9.819765 | 14.25 | 15.56039 |
| #2 | 8.75 | 5.714286 | 11.75 | 23.43647 |
| #3 | 13.25 | 11.32075 | 14.75 | 10.16949 |
| #4 | 12.5 | 10.32796 | 13.25 | 7.225865 |
| #5 | 13.75 | 12.42055 | 14.25 | 3.508772 |
| #6 | 11 | 16.59765 | 13.75 | 19.12695 |
| #7 | 13.25 | 16.73476 | 16 | 26.02082 |
| #8 | 16 | 29.3151 | 15 | 19.62614 |
| #9 | 12.25 | 13.94143 | 11.75 | 8.148316 |
| #10 | 10.5 | 19.82539 | 9.75 | 21.14413 |
| #11 | 15.25 | 18.83463 | 16 | 5.103104 |

As shown on Table 2, the 1 step configuration had a smaller half-value width, thereby having a greater resolution. It is deduced that a smoother transfer of the sample from the sample containing gel to the sample separating gel attributes to the smaller half-value width and the greater resolution. Simulation (not shown) showed no difference between the 1 step configuration and the 2 step configuration.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

Moreover, the entire contents of all the non-patent literatures an patent literatures cited in the Description of the present application are incorporated herein by reference.

INDUSTRIAL APPLICABILITY

The present invention, capable of providing a solution to the drawbacks of the 2-dimensional electrophoresis apparatus, can facilitate proteome researches performed recently with ardency. By producing and selling various components for use in electrophoresis apparatus according to the present invention, it is possible to stimulate markets.

| Reference Signs List | |
|---|---|
| 100, 200: | Electrophoresis apparatus |
| 101: | Sample separating section |
| 102: | First plate |
| 103: | Second plate |
| 203, 204: | Acrylic plate |
| 104: | First buffer tank |
| 105: | Second buffer tank |
| 106: | Communicating opening |
| 107, 206: | Holding section |
| 108: | Transporting arm |
| 109: | Recess section (first engaging section) |
| 110: | Recess section (section engaging section) |
| 120: | Seal for medium shaping |
| 130: | Cap for medium shaping |
| 131: | Protrusion section (third engaging section) |
| 132: | Protrusion section (fourth engaging section) |
| 150, 205: | Sample separating medium |
| 151: | Exposed portion |
| 152: | Bulged portion |
| 153: | Supporting section |
| 160, 207: | Sample containing medium |
| 161: | Sample containing medium storage site |

The invention claimed is:

1. An electrophoresis apparatus, comprising:
a sample separating section for containing a sample separating medium for separating a sample in a horizontal direction, the sample separating section containing the sample separating medium in such a manner that the sample separating medium has an exposed portion at at least one end of a surface of the sample separating medium, the surface being in parallel with the horizontal direction; and
medium connecting means for connecting a sample containing medium to the sample separating medium at a connecting region at the exposed portion, the sample containing medium containing a sample
a first buffer tank containing at least part of the exposed portion;
a second buffer tank being located in such a manner that the sample separating section will be in between the second buffer tank and the exposed portion, the sample separating section having a communicating opening for communicating between the sample separating medium and the second buffer tank;
a cap for medium shaping, the cap being detachably provided so as to cover the exposed portion of the sample separating medium in the first buffer tank; and
a seal for medium shaping, the seal sealing the communication opening;
wherein:
the sample separating section has a first engaging section and the cap has a third engaging section, wherein the first engaging section and the third engaging section are configured to engage together, and
the first buffer tank has a second engaging section and the cap has a fourth engaging section, wherein the second engaging section and the fourth engaging section are configured to engage together.

2. An electrophoresis apparatus as set forth in claim 1, wherein:
the sample separating medium has a supporting section whose top reaches a height equal to or higher than the inside end of the exposed portion, and
the connecting region is on the supporting section.

3. An electrophoresis apparatus as set forth in claim 1, wherein:
the sample separating section has two plates being parallel with each other, for holding the sample separating medium therebetween.

4. An electrophoresis apparatus as set forth in claim 1, wherein:
the sample containing medium and the sample separating medium are a gel or gels that contain(s) a gelling agent selected from the group consisting of polyacrylic amides, agarose, agar, and starch.

5. An electrophoresis apparatus as set forth in claim 1, wherein:
the sample containing medium is higher in viscoelasticity than the sample separating medium.

6. An electrophoresis apparatus as set forth in claim 1 comprising a structure in which the sample separating section, the first buffer tank, and the second buffer tank are integrated.

7. An electrophoresis apparatus as set forth in claim wherein:
the first buffer tank and the cap are configured such that, when the cap is attached inside the first buffer tank, the first buffer tank still has a space for holding a liquid.

8. An electrophoresis apparatus as set forth in claim 1, wherein:
the cap has an overlapping section for being overlapped with a surface of the sample separating section or a side wall of the first buffer tank.

9. An electrophoresis apparatus as set forth in claim 8, wherein:
the overlapping section has an overlapping width of at least 1 mm.

10. An electrophoresis apparatus, as set forth in claim 1, wherein:
the communicating opening is located on an upper surface of the sample separating section.

11. An electrophoresis apparatus as set forth in claim 1, wherein:
the sample separating medium having a bulged portion being bulged downward and located on a distal side to the exposed portion and in a region ranged from the communicating opening to an edge of the sample separating medium.

12. A method of performing electrophoresis, comprising:
connecting a sample separating medium with a sample containing medium at a connecting region, (i) the sample separating medium being configured to separate a sample in a horizontal direction and being held in an insulating member in such a manner that the separating medium has an exposed portion at at least one end of a surface of the sample separating medium, (ii) the sample containing medium containing the sample, being exposed at the exposed portion;
the sample separating medium being part of an electrophoresis apparatus
further comprising:
a first buffer tank containing at least part of the exposed portion;
a second buffer tank being located in such a manner that the sample separating section will be in between the second buffer tank and the exposed portion, the sample separating section having a communicating opening for communicating between the sample separating medium and the second buffer tank;
a ca for medium shaping, the cap being detachably provided so as to cover the exposed portion of the sample separating medium in the first buffer tank; and
a seal for medium shaping, the seal sealing the communication opening;
wherein:
the sample separating section has a first engaging section and the can a third engaging section, wherein the first engaging section and the third engaging section are configured to engage together, and
the first buffer tank has a second engaging section and the cap has a fourth engaging section, wherein the second engaging section and the fourth engaging section are configured to engage together.

13. The method of claim 12, wherein:
the sample separating medium has a supporting section whose top reaches a height equal to or higher than the inside end of the exposed portion, and
the connecting region is on the supporting section.

14. An electrophoresis apparatus, comprising:
a sample separating section for containing a sample separating medium for separating a sample in a horizontal direction, the sample separating section containing the sample separating medium in such a manner that the sample separating medium has an exposed portion at at least one end of a surface of the sample separating medium, the surface being in parallel with the horizontal direction; and
medium connecting means for connecting a sample containing medium to the sample separating medium at a connecting region, the sample containing medium containing a sample, and the connecting region satisfying the following equation (1):

$$Y \geq 0.4 \times X \qquad (1),$$

where X is a distance in the horizontal direction from an inside end of the exposed portion exposed on an upper surface of the sample separating medium, to an inside end of the sample containing medium, and Y is a distance from the upper surface of the sample separating medium to an upper surface of the sample containing medium downwardly in a vertical direction;
a first buffer tank containing at least part of the exposed portion;
a second buffer tank being located in such a manner that the sample separating section will be in between the second buffer tank and the exposed portion, the sample separating section having a communicating opening for communicating between the sample separating medium and the second buffer tank;
a cap for medium shaping, the cap being detachably provided so as to cover the exposed portion of the sample separating medium in the first buffer tank; and
a seal for medium shaping, the seal sealing the communication opening;
wherein:
the sample separating section has a first engaging section and the cap has a third engaging section, wherein the first engaging section and the third engaging section are configured to engage together, and
the first buffer tank has a second engaging section and the cap has a fourth engaging section, wherein the second engaging section and the fourth engaging section are configured to engage together.

15. An electrophoresis apparatus as set forth in claim 14, wherein:
the first engaging section and the third engaging section are configured to engage with each other by being configured that the first engaging section has a protrusion section and the third engaging section has a recess section corresponding to the protrusion section, or by being configured that the first engaging section has a recess section and the third engaging section has a protrusion section corresponding to the recess section,
the second engaging section and the fourth engaging section are configured to engage with each other by being configured that the second engaging section has a protrusion section and the fourth engaging section has a recess section corresponding to the protrusion section, or by being configured that the second engaging section has a recess section and the fourth engaging section has a protrusion section corresponding to the recess section, and the engagement between the first engaging section and the third engaging section is different in depth from the engagement between the second engaging section and the fourth engaging section.

* * * * *